(12) United States Patent
Artiss (10) Patent No.: US 11,660,283 B2
(45) Date of Patent: May 30, 2023

(54) CANNABINOID-CONTAINING COMPOSITION

(71) Applicant: Joyn Botanicals Ltd., Windsor (CA)

(72) Inventor: Joseph D Artiss, Windsor (CA)

(73) Assignee: Joyn Botanicals Ltd., Windsor (CA)

( * ) Notice: Subject to any disclaimer, the term of this patent is extended or adjusted under 35 U.S.C. 154(b) by 3 days.

(21) Appl. No.: 16/225,964

(22) Filed: Dec. 19, 2018

(65) Prior Publication Data

US 2020/0197353 A1 Jun. 25, 2020

(51) Int. Cl.
| | | |
|---|---|---|
| *A61K 31/352* | (2006.01) | |
| *A61K 31/05* | (2006.01) | |
| *A61P 25/24* | (2006.01) | |
| *A61P 25/28* | (2006.01) | |
| *A23L 33/105* | (2016.01) | |
| *A23L 29/269* | (2016.01) | |
| *A61K 36/185* | (2006.01) | |

(52) U.S. Cl.
CPC .......... *A61K 31/352* (2013.01); *A23L 29/273* (2016.08); *A23L 33/105* (2016.08); *A61K 31/05* (2013.01); *A61K 36/185* (2013.01); *A61P 25/24* (2018.01); *A61P 25/28* (2018.01); *A23V 2002/00* (2013.01); *A23V 2200/31* (2013.01); *A23V 2200/32* (2013.01); *A23V 2250/2132* (2013.01); *A23V 2250/5112* (2013.01)

(58) Field of Classification Search
None
See application file for complete search history.

(56) References Cited

U.S. PATENT DOCUMENTS

| | | |
|---|---|---|
| 6,890,549 B2 | 5/2005 | Artiss et al. |
| 7,423,026 B2 | 9/2008 | Jaervinen et al. |
| 7,592,328 B2 | 9/2009 | Jarho et al. |
| 8,735,374 B2 | 5/2014 | Zerbe et al. |
| 8,895,078 B2 | 11/2014 | Mueller |
| 10,058,531 B1 | 8/2018 | Chistov |
| 2005/0153931 A1 | 7/2005 | Jarho et al. |
| 2014/0271940 A1* | 9/2014 | Wurzer .............. A61P 25/00 424/725 |
| 2016/0324776 A1 | 11/2016 | Glatzel |
| 2017/0020945 A1 | 1/2017 | Reillo et al. |
| 2017/0224842 A1* | 8/2017 | Czap .............. A61K 36/185 |
| 2018/0069078 A1 | 3/2018 | Reillo et al. |
| 2018/0085308 A1 | 3/2018 | Renwick et al. |
| 2018/0116240 A1 | 5/2018 | Docherty et al. |
| 2018/0117161 A1 | 5/2018 | Docherty et al. |

FOREIGN PATENT DOCUMENTS

| | | |
|---|---|---|
| CN | 109953951 A | 7/2019 |
| CN | 110496064 A | 11/2019 |
| WO | WO 00/25127 A1 | 5/2000 |
| WO | WO 03/070774 A1 | 8/2003 |
| WO | WO 2015/022454 A1 | 2/2015 |
| WO | WO 2017/180954 A1 | 10/2017 |
| WO | WO 2017/183011 A1 | 10/2017 |
| WO | WO 2018/058235 A1 | 4/2018 |
| WO | WO 2020/161715 A1 | 8/2020 |
| WO | WO 2020/161715 A9 | 8/2020 |

OTHER PUBLICATIONS

International Search Report (PCT/ISA/210) issued in PCT Application No. PCT/IB2019/060799 dated Mar. 4, 2020 (nine (9) pages).
Written Opinion (PCT/ISA/237) issued in PCT Application No. PCT/IB2019/060799 dated Mar. 4, 2020 (nine (9) pages).
Lv et al., "Structural analysis and cytotoxicity of host-guest inclusion complexes of cannabidiol with three native cyclodextrins," Journal of Drug Delivery Science and Technology, 2019, pp. 337-344, vol. 51 (8 pages).
Hazekamp et al., "Structure elucidation of the tetrahydrocannabinol complex with randomly methylated β-cyclodextrin", European Journal of Pharmaceutical Sciences, 2006, pp. 340-347, vol. 29 (eight (8) pages).
Morales et al., "An Overview on Medicinal Chemistry of Synthetic and Natural Derivatives of Cannabidiol", Frontiers in Pharmacology, Jun. 2017, pp. 1-18, vol. 8, Article 422 (18 pages).
Shoyama et al., "Cannabis XV Preparation and Stability of $\Delta^9$-Tetrahyrocannabinol-β-Cyclodextrin Inclusion Complex", Journal of Natural Products, 1983, pp. 633-637, vol. 46, No. 5 (five (5) pages).
Mannila et al., "Precipitation Complexation Method Produces Cannabidiol/β-Cyclodextrin Inclusion Complex Suitable for Sublingual Administration of Cannabidiol", Journal of Pharmaceutical Sciences, Feb. 2007, pp. 312-319, vol. 96, No. 2 (eight (8) pages).
Mannila et al., "Sublingual administration of $\Delta^9$-Tetrahyrocannabinol/β-Cyclodextrin complex increases the bioavailability of $\Delta^9$-Tetrahydrocannabinol in rabbits", Life Sciences, 2006, pp. 1911-1914, vol. 78 (four (4) pages).
Bochot et al., "α-Cyclodextrin/Oil Beads: An Innovative Self-Assembling System", International Journal of Pharmaceutics, 2007, pp. 121-129, vol. 339, (nine (9) pages).
Trichard et al., "Novel Beads Made of Alpha-Cyclodextrin and Oil for Topical Delivery of a Lipophilic Drug", Pharmaceutical Research, Feb. 2008, pp. 435-440, vol. 25, No. 2, (six (6) pages).

(Continued)

*Primary Examiner* — Terry A McKelvey
*Assistant Examiner* — Catheryne Chen
(74) *Attorney, Agent, or Firm* — Crowell & Moring LLP (57) ABSTRACT

The invention relates to compositions comprising complexes of α-cyclodextrin and cannabinoids and/or complexes of α-cyclodextrin and terpenes, methods of making these α-cyclodextrin and cannabinoid complex-containing compositions, and methods of using the α-cyclodextrin and cannabinoid complex-containing compositions. The invention also relates to food products comprising the α-cyclodextrin and cannabinoid complex-containing compositions of this invention.

10 Claims, 4 Drawing Sheets

(4 of 4 Drawing Sheet(s) Filed in Color)

(56) References Cited

OTHER PUBLICATIONS

Shimada et al., "Structure of Inclusion Complexes of Cyclodextrins with Triglyceride at Vegetable Oil/Water Interface", Journal of Food Science, 1992, pp. 655-656, vol. 57, No. 3, (two (2) pages).
Bisson-Boutelliez et al., "Preparation and Physicochemical Characterization of Amoxicillin β-Cyclodextrin Complexes", AAPS PharmSciTech, Jun. 2010, pp. 574-581, vol. 11, No. 2, (eight (8) pages).
Cheirsilp et al., "Inclusion Complex Formation of Cyclodextrin with Its Guest and Their Applications", Biology, Engineering and Medicine, 2016, pp. 1-6, vol. 2, No. 1, (six (6) pages).
Wadhwa et al., "Essential Oil—Cyclodextrin Complexes: An Updated Review", J Incl Phenom Macrocycl Chem, 2017, pp., vol. 89, No. 39-58, (20 pages).
Maazaoui et al., "Applications of Cyclodextrins: Formation of Inclusion Complexes and Their Characterization", International Journal of Advanced Research, 2015, pp. 758-781, vol. 3, No. 2, (25 pages).
Harada et al., "Preparation and Properties of Inclusion Complexes of Poly(ethylene glycol) with α-Cyclodextrin", Macromolecules, 1993, pp. 5698-5703, vol. 26, (six (6) pages).
Bhopate et al., "Preparation and Characterization of β-Cyclodextrin Nebivolol Inclusion Complex", International Journal of Pharmaceutical Sciences and Research, 2015, pp. 2205-2213, vol. 6, No. 5, (nine (9) pages).
Al-Marzouqi et al., "Physicochemical Properties of Antifungal Drug—Cyclodextrin Complexes Prepared by Supercritical Carbon Dioxide and by Conventional Technigues", Journal of Pharmaceutical and Biomedical Analysis, 2009, pp. 227-233, vol. 49, (seven (7) pages).
Szejtli J., "Past, Present, and Future of Cyclodextrin Research", Pure Appl. Chem., 2004, pp. 1825-1845, vol. 76, No. 10, (21 pages).
Jambhekar et al., "Cyclodextrins in Pharmaceutical Formulations I: Structure and Physicochemical Properties, Formation of Complexes, and Types of Complex", Drug Discovery Today, Feb. 2016, pp. 356-362, vol. 21, No. 2, (seven (7) pages).
Yoshii et al., "Formation of Inclusion Complexes of Cycldextrin with Ethanol Under Anhydrous Conditions", Biosci. Biotechnol. Biochem., 1998, pp. 2166-2170, vol. 62, No. 11, (five (5) pages).
Extended European Search Report issued in European Application No. 19899721.5 dated Jul. 14, 2022 (nine (9) pages).
S. R. Sommano et al. "The Cannabis Terpenes", Molecules, vol. 25, No. 24, p. 5792, XP055939121 dated Dec. 8, 2020 (16 pages).
International Preliminary Report on Patentability (PCT/IB/326 & PCT/IB/373), including Written Opinion (PCT/ISA/237) issued in PCT Application No. PCT/IB2019/060799 dated Jul. 1, 2021 (11 pages).
Brenneisen, "Chemistry and Analysis of Phytocannabinoids and Other Cannabis Constituents", Forensic Science and Medicine: Marijuana and the Cannabinoids, 2010, pp. 17-49, Totowa, New Jersey, (33 pages).
McGowan et al., "A Peroxidase-Coupled Method for the Colorimetric Determination of Serum Triglycerides", Clinical Chemistry, 1983, pp. 538, vol. 29, No. 3, (five (5) page).
Romano et al., "Cannabis Oil: Chemical Evaluation of an Upcoming Cannabis-Based Medicine", Cannabinoids, 2013, vol. 1, No. 1, pp. 1-11, (six (6) pages).
Kiss et al., "Evaluation of the Cytotoxicity of β-Cyclodextrin Derivatives: Evidence for the Role of Cholesterol Extraction", European Journal of Pharmaceutical Sciences, 2010, pp. 376-380, vol. 40, (five (5) pages).

\* cited by examiner

CANNABINOID-CONTAINING COMPOSITION

BACKGROUND

*Cannabis* contains more than 500 compounds, including at least 66 cannabinoids that are unique to *Cannabis* and at least 140 terpenes that are widespread throughout the plant kingdom. (Brenneisen, R., Chemistry and Analysis of Phytocannabinoids and Other *Cannabis* Constituents, in Forensic Science and Medicine: Marijuana and the Cannabinoids. Ed. El Sohly, Mass. Humana Press Inc., Totowa, N.J. Chapter 2, pgs. 17-49. 2010.)

The term "phytocannabinoid" has been proposed to differentiate naturally-occurring cannabinoids from synthetically produced cannabinoids. Synthetically produced cannabinoids are cannabinoid compounds that are made synthetically in laboratories. Phytocannabinoids are all $C_{21}$ terpenophenolic compounds, of which tetrahydrocannabinol (THC) and cannabidiol (CBD) are perhaps the most studied and best understood for their therapeutic and recreational value. However, phytocannabinoids as a whole have become of interest for the treatment of various disorders and disease states, such as anxiety disorders, depression, cachexia, various forms of pain (e.g., acute pain, chronic pain, neuropathic pain, trigeminal nerve pain, and pain associated with or accompanying migraine headaches and cancer).

The 140 terpenes that are present in *Cannabis* include monoterpenoids, sesquiterpenoids, diterpenoids, and triterpenoids. (Brenneisen, pgs. 17-49.) For the most part, these terpenes are hydrophobic and comprise short aliphatic branched chains or substituted monocyclic compounds. Terpenes present in *Cannabis* are responsible for the unpleasant turpentine or pine needle tastes and odors that are common to *cannabis* plant extracts.

Naturally-occurring cyclodextrins are cyclic polymers of glucose units that are formed by the enzymatic action of specific cyclodextrin glycosyltransferases (CGT) on partially-hydrolyzed corn starch. Depending on the CGT used, cyclic polymers of six, seven, or eight glucose units are produced, which are respectively named α-cyclodextrin, β-cyclodextrin, and γ-cyclodextrin. The size of the cyclodextrin molecule, and therefore the "pore" formed by the cyclodextrin molecule, is dictated by the number of glucose units in the polymer. Thus, α-cyclodextrin has the smallest pore, while γ-cyclodextrin has the largest. α-cyclodextrin is known to sequester small molecules (e.g., fatty acids, nitrobenzene) (McGowan, M. et al., A peroxidase-coupled method for the colorimetric determination of serum triglycerides. Clin. Chem. 1983, 29, 538-542), while β-cyclodextrin and γ-cyclodextrin sequester larger poly- and heterocyclic compounds (e.g., cholesterol, THC or CBD).

Shoyama describes a method for the preparation of pure THC and β-cyclodextrin complexes and demonstrates that these complexes are stable. (Shoyama Y. et al., Preparation and stability of $\Delta^9$-tetrahydrocannabinol-β-cyclodextrin inclusion complex, J. Nat. Prod. 1983, 46(5), 633-637.) Hazekamp assess the water solubility of pure THC in the presence of α-cyclodextrin, β-cyclodextrin, γ-cyclodextrin, and randomly methylated-β-cyclodextrins and states that only the randomly methylated-β-cyclodextrins increase the water solubility of THC. (Hazekamp, A. et al., Structure elucidation of the tetrahydrocannabinol complex with randomly methylated β-cyclodextrin, Eur. J. Pharm. Sci. 2006, 29, 340-347.) Mannila et al. describe the preparation of β-cyclodextrin complexes with CBD for the sublingual administration of CBD and the preparation of methylated-cyclodextrin complexes with CBD and THC. (U.S. Pat. No. 7,592,328; Mannila J. et al., Precipitation complexation method produces cannabidiol/β-cyclodextrin inclusion complex suitable for sublingual administration of cannabidiol, J. Pharm. Sci. 2007, 96(2), 312-319.) U.S. Pat. No. 7,423,026 describes methylated β-cyclodextrin complexes with cannabinol, THC, and CBD. U.S. Pat. No. 8,735,374 describes the preparation of an oral mucoadhesive dosage form of THC and γ-cyclodextrin and a mixture of THC and CBD with a mixture that includes both β- and γ-cyclodextrin.

U.S. Patent No. 2017/0224842 ("Czap") describes γ-cyclodextrin complexes of cannabinoids from partially purified, low terpene containing, hemp oil. In order to release the guest cannabinoid molecule from the host cyclodextrin and to alleviate the concerns surrounding undigested cyclodextrins, Czap's complexes are formulated with amylase-like enzymes that hydrolyze the cyclodextrin. Czap further discloses that a mixture of cyclodextrins may be used to sequentially form inclusion complexes with different size molecules. Czap's formulation must be kept dry to prevent premature activation of the amylase-like enzymes. Thus Czap's formulation is not feasible for use in beverages, food stuffs, and confections. Furthermore, hot beverages or a baking process will likely denature the amylase-like enzymes in Czap's complexes.

WO 2017/180954 describes the emulsification of specific cannabinoids with a mixture of at least two emulsifiers, including a synthetic β-cyclodextrin. WO 2018/058235 describes the preparation of a complex using *cannabis* plant extract, β-cyclodextrin, and other ingredients (e.g., release-modifying agents and excipients for use in a time-released tablet).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A depicts a graduated cylinder containing 100 mL water mixed with 863 mg of a dried *cannabis* plant extract composition comprising 1 mg THC and α-cyclodextrin (final concentration, 10 mg/L THC). The concentration of THC in the aqueous mixture was 10 mg/L. FIG. 4B depicts a graduated cylinder containing 100 mL water without the addition of the THC/α-cyclodextrin-containing *cannabis* plant extract.

DESCRIPTION OF THE INVENTION

Described herein is method for preparing a composition comprising water soluble complexes of α-cyclodextrin and a cannabinoid by mixing one or more cannabinoids with an aqueous α-cyclodextrin-containing composition under conditions wherein the α-cyclodextrin forms complexes with the cannabinoids. The cannabinoids may be a phytocannabinoids, i.e., naturally-occurring cannabinoids, or a synthetically produced cannabinoids referred to hereinafter as "synthetic cannabinoids." An embodiment of this invention is a method for preparing a *cannabis* plant-derived composition, by treating a *cannabis* plant extract with an aqueous α-cyclodextrin-containing composition under conditions wherein the α-cyclodextrin forms complexes with the cannabinoids and terpenes in the plant extract thereby producing the *cannabis* plant extract derived composition. Another embodiment of this invention is method for preparing a synthetic cannabinoid-derived composition comprising water soluble complexes of α-cyclodextrin and synthetic cannabinoids, by mixing a composition comprising synthetic cannabinoids with an aqueous α-cyclodextrin-containing composition under conditions wherein the α-cyclodextrin forms complexes with the synthetic cannabinoids thereby producing the synthetic cannabinoid-derived composition.

Also described herein is a *cannabis* plant extract-derived composition comprising complexes of α-cyclodextrin and at least one cannabinoid, or complexes of α-cyclodextrin and at least one terpene, or both complexes of α-cyclodextrin and at least one cannabinoid and complexes of α-cyclodextrin and at least one terpene. The cannabinoids may be, e.g., THC, CBD, cannabinol, or mixtures thereof.

Also described herein is a composition comprising complexes of α-cyclodextrin and at least one synthetic cannabinoid. Synthetic cannabinoids are well known in the art and include, e.g., 1-pentyl-3-(1-naphthoyl)indole (JWH-018), 1-butyl-3-(1-naphthoyl)indole (JWH-073), 1-[2-(4-morpholinyl)ethyl]-3-(1-naphthoyl)indole (JWH-200), 5-(1,1-dimethylheptyl)-2-[(1R, 3 S)-3-hydroxycyclohexyl]-phenol (CP-47,497), and 5-(1,1-dimethyloctyl)-2-[(1R, 3 S)-3-hydroxycyclohexyl]-phenol (cannabicyclohexanol; CP-47,497 C8 homologue) and other CBD analogs (see e.g., Morales et al. Frontiers in Pharmacology 28 Jun. 2017 Vol 8, Article 422 p. 1-18). Synthetic cannabinoids also include the FDA approved compounds dronabinol, a synthetic delta-9-tetrahydrocannabinol (THC), and nabilone, which has a chemical structure similar to THC and is synthetically derived.

The compositions of this invention, e.g., the *cannabis* plant extract-derived composition and synthetic cannabinoid-derived compositions comprising complexes of α-cyclodextrin and cannabinoids and/or complexes of α-cyclodextrin and terpenes, exhibit reduced or no odor and/or taste associated with cannabinoids or terpenes, as compared to the starting material, e.g. a *cannabis* plant extract or synthetic cannabinoid. Moreover, the compositions of this invention achieve the effects associated with administration of cannabinoids, e.g., reduction in symptoms of pain or anxiety, or an increase in feelings of well-being, more rapidly than achieved with the starting material, e.g., the untreated *cannabis* plant extract or synthetic cannabinoid. These effects are also prolonged as compared to the effects achieved with the untreated material. Without wishing to be bound by theory it is contemplated that the α-cyclodextrin and cannabinoids complexes are amphiphilic complexes, having a hydrophilic or polar end and a hydrophobic or nonpolar end, that are absorbed quickly through mucosal membranes such that the cannabinoids are absorbed into the blood stream of the subject more quickly as compared to the uncomplexed cannabinoids. The compositions of this invention comprising the complexes of α-cyclodextrin and cannabinoids, and/or complexes of α-cyclodextrin and terpenes may be in the form of, e.g., a powder, an aqueous solution, an aqueous slurry, or an aqueous suspension. The powder, aqueous solution, uniform aqueous slurry and uniform aqueous suspension offer the added benefit of controlled and consistent dosing of the cannabinoids contained therein.

It has been discovered that α-cyclodextrin renders phytocannabinoids and terpenes in *cannabis* plant extracts, and synthetic cannabinoids having aliphatic chains long enough to complex with α-cyclodextrin, soluble in aqueous medium. Without wishing to be bound by theory, it is contemplated that the terpenes form complexes with the α-cyclodextrin and the aliphatic chains of cannabinoids are long enough to form a complex with α-cyclodextrin. Thus, α-cyclodextrin eliminates the terpene taste and odor characteristic of *cannabis* plant extracts, e.g., *cannabis* oil or *cannabis* tar, and renders the cannabinoids and terpenes in the compositions of this invention soluble in an aqueous medium.

The *cannabis* plant that serves as the source of the plant extract from which the inventive compositions are derived may be, e.g., a *Cannabis sativa, Cannabis indica* or *Cannabis ruderalis*, hemp, and strains and hybrid varieties, including crossbred varieties, of such *cannabis* plants. In an embodiment the *cannabis* plant is not hemp, e.g., a *cannabis* plant having a THC content of less than or equal to 0.2% or less than or equal to 0.3% of the dried flowering portion of the plant. In some embodiments the extract is from a *cannabis* plants having a THC content of the dried flowering portion of the plant of less than or equal to 0.3%. In some embodiments the *cannabis* plant is marijuana. In some embodiments the extract is from a *cannabis* plants having a THC content of the dried flowering portion of the plant of greater than 0.3%. In embodiments of this invention the extract is prepared from a *cannabis* plant having greater than 0.3% to about 30% and in some embodiments the THC content of the dried flowering portion of the plant is about 5% to about 30% or about 5% to about 20% of the dried flowering portion of the plant.

In addition to the commercially available *cannabis* plant extracts comprising cannabinoids that are suitable for use in the methods of this invention, those of skill in the art recognize that there are a variety of extraction methods, e.g., solvent extraction, and $CO_2$ extraction, known in the art for producing a *cannabis* plant extract comprising cannabinoids, or an extract comprising cannabinoids and terpenes, that are suitable for use in the methods of this invention. Some of the known methods produce *cannabis* plant extracts containing high levels of THC, in some instances as high as 80%, 90% or more (see e.g., Romano and Hazekamp Cannabinoids 2013:1(1):1-11, U.S. Pat. No. 8,895,078, and WO 00/25127, incorporated herein by reference in their entirety). In some embodiments the *cannabis* plant extract is treated to increase the ratio of cannabinoids to terpenes, e.g. by reducing the amount of terpenes and/or increasing the concentration of cannabinoids. For example, the *cannabis* plant extract may be subjected to purification techniques known in the art, such as distillation, chromatography, or crystallization to obtain a composition high in cannabinoid content with a reduced level of terpenes. A benefit of using an unpurified *cannabis* plant extract to produce the composition of this invention is that the resulting composition contains a broad spectrum, if not all, of the medicinally beneficial cannabinoids of the starting *cannabis* plant extract.

One embodiment of the invention is a method for making a *cannabis* plant-derived composition comprising α-cyclodextrin and a compound selected from cannabinoids, terpenes, or mixtures thereof, the method comprising the steps of: (a) combining a *cannabis* plant extract comprising at least one cannabinoid and/or at least one terpene with an aqueous α-cyclodextrin-containing composition, e.g., an aqueous α-cyclodextrin solution, an aqueous α-cyclodextrin slurry, or an aqueous α-cyclodextrin suspension; and (b) mixing the *cannabis* plant extract and the aqueous α-cyclodextrin composition for a sufficient time to form a complex between the α-cyclodextrin and the cannabinoid(s) and/or terpene(s), thereby producing an aqueous mixture comprising complexes of α-cyclodextrin and a compound selected from cannabinoids, terpenes, and/or mixtures thereof. The method may further comprise the step of (c) drying the mixture from step (b), thereby producing a *cannabis* plant extract-derived composition comprising complexes of α-cyclodextrin and at least one cannabinoid, or complexes of α-cyclodextrin and at least one terpene, or mixtures of complexes of α-cyclodextrin and at least one cannabinoid and complexes of α-cyclodextrin and at least one terpene, in the form of an odorless and/or tasteless water-soluble powder. Suitable methods for drying the mixture include evaporating the mixture in dishes or pans, evaporating under reduced pressure and/or ambient temperatures and/or moderately elevated temperatures (e.g., temperatures ranging from 40-150° C.), evaporating in a rotary evaporator, freeze drying or lyophilization, spray drying, or by any other drying method known to a person of skill in the art. This method may also be applied to a synthetic cannabinoid containing composition rather than a *cannabis* plant extract to produce a synthetic cannabinoid-derived composition comprising complexes of α-cyclodextrin and one or more synthetic cannabinoids.

The *cannabis* plant extract or synthetic cannabinoids and the aqueous α-cyclodextrin-containing composition are mixed together for a length of time sufficient to form complexes between the α-cyclodextrin and the cannabinoid(s) and/or terpene(s), e.g., at least 5 minutes, at least 15 minutes, at least 30 minutes, at least 45 minutes, at least 1 hour, at least 3 hours, at least 6 hours, or at least 12 hours. The *cannabis* plant extract or synthetic cannabinoids and the aqueous α-cyclodextrin containing composition are mixed together under conditions wherein an emulsion is not formed. In one embodiment, the synthetic cannabinoid-derived composition of this invention comprising complexes of α-cyclodextrin and the synthetic cannabinoids is not an emulsion.

Suitable aqueous α-cyclodextrin-containing compositions for mixing with the *cannabis* plant extract or synthetic cannabinoids in the methods described herein comprise at least 15% w/v α-cyclodextrin. Preferable α-cyclodextrin slurries or suspensions comprise at least 20% w/v α-cyclodextrin. Preferable α-cyclodextrin slurries or suspensions comprise at least 25% w/v α-cyclodextrin. Suitable aqueous α-cyclodextrin slurries or suspensions comprise an amount of α-cyclodextrin that exceeds the solubility of α-cyclodextrin in the solution such that non-solubilized α-cyclodextrin is present in the slurry or suspension. In an embodiment of this invention the aqueous α-cyclodextrin compositions for mixing with the *cannabis* plant extract or synthetic cannabinoids comprises about 15% w/v to about 40% w/v α-cyclodextrin, about 20% w/v to about 35% w/v α-cyclodextrin or about 20% to about 30% w/v α-cyclodextrin.

It is recognized that the amount of α-cyclodextrin to be mixed with the *cannabis* plant extract or synthetic cannabinoids to complex with the cannabinoids and terpenes may be varied depending on the characteristics of the starting material, e.g., its viscosity, its solids content, its cannabinoid content, or its terpene content, and the desired characteristics of the composition produced by the methods described herein, e.g., a solution, a powder, or a slurry. In an embodiment of the invention the ratio of α-cyclodextrin to the *cannabis* plant extract is at least about 70:1 weight/weight (w/w), at least about 80:1 w/w, at least about 85:1 w/w, at least about 95:1 w/w or at least about 100:1 w/w, at least about 120:1 and ranges there between.

In one embodiment of the invention, the aqueous α-cyclodextrin-containing composition, e.g. a solution, slurry, or suspension, is combined with the *cannabis* plant extract or synthetic cannabinoids in an amount and mixed for a time and at a temperature such that at least 80%, at least 85%, at least 90%, at least 95%, at least 99%, or at least 100% of the cannabinoids are complexed with the α-cyclodextrin.

In one embodiment of the invention, the aqueous α-cyclodextrin-containing composition, e.g., a solution, slurry, or suspension, is combined with the *cannabis* plant extract in an amount such that at least 80%, at least 85%, at least 90%, at least 95%, at least 99%, or at least 100% of the terpenes are complexed with the α-cyclodextrin.

In one embodiment of the invention, the aqueous α-cyclodextrin-containing composition, e.g., solution, slurry, or suspension, is combined with the *cannabis* plant extract or synthetic cannabinoids in an amount such that at least 80%, at least 85%, at least 90%, at least 95%, at least 99%, or at least 100% of the cannabinoids and terpenes are complexed with the α-cyclodextrin.

In an embodiment of this invention, to achieve the *cannabis* plant extract-derived composition or synthetic cannabinoid-derived composition of this invention having essentially no odor or taste typically associated with a cannabinoid, the ratio of α-cyclodextrin to cannabinoids in the extract or synthetic cannabinoid is greater than about 70:1 w/w, greater than 85:1 w/w, greater than 90:1 w/w, greater than 95:1 w/w, greater than about 100:1 w/w and greater than about 120:1 w/w and ranges there between.

U.S. Patent No. 2017/0224842 (Czap) describes mixing cyclodextrin with cannabinoids from partially purified, low terpene containing, hemp oil. Unlike the Czap formulations, which are formulated with amylase-like enzymes that hydrolyze the cyclodextrins, the *cannabis* plant extract-derived compositions and synthetic cannabinoid-derived composition of this invention, do not require an amylase-like enzyme to be effective and achieve their desired results. Thus an aspect of this invention is a *cannabis* plant extract-derived compositions or synthetic cannabinoid-derived composition comprising complexes of α-cyclodextrin and a compound selected from cannabinoids, terpenes, or mixtures thereof, wherein the compositions do not comprise an amylase or an amylase-like enzyme, e.g., a cyclodextrinase, maltogenic amylase, or neopullulanase, that is formulated so that the cyclodextrin-degrading activity of the enzyme is activated on delivery of the composition to a subject.

In one embodiment, the plant extract-derived compositions of this invention comprise α-cyclodextrin complexes comprising THC, CBD, cannabinol, or mixtures thereof. In an embodiment of the invention, the cannabinoids in complex with α-cyclodextrin are selected from the group consisting of THC, CBD, cannabinol, and mixtures thereof.

Preferably the *cannabis* plant extract and synthetic cannabinoids (or compositions comprising synthetic cannabinoids) have a consistency that facilitates its mixing with the aqueous α-cyclodextrin-containing composition. For example, the *cannabis* plant extract and synthetic cannabinoids may have the consistency of a free flowing oil. Thus, in an embodiment of this invention, the *cannabis* plant extract or synthetic cannabinoid is mixed with a solvent to facilitate its mixing with an aqueous α-cyclodextring containing composition. The solvent may be for example water, an oil, or an alcohol. The amount of solvent added to the *cannabis* plant extract or synthetic cannabinoid is sufficient such that the *cannabis* plant extract or synthetic cannabinoid is free flowing. The amount of solvent added to the *cannabis* plant extract or synthetic cannabinoid may be up to 95% v/v of the total volume of the solvent and *cannabis* plant extract mixture. The amount of solvent added to the *cannabis* plant extract or synthetic cannabinoid is preferably up to 75% v/v. The amount of solvent added to the *cannabis* plant extract or synthetic cannabinoid is more preferably up to 50% v/v. The extract or synthetic cannabinoid may be mixed with the solvent before or after, preferably before, combining the extract or synthetic cannabinoid with an aqueous α-cyclodextrin-containing composition. Preferably the solvent is mixed with the extract or synthetic cannabinoid before combining the extract or synthetic cannabinoid with the aqueous cyclodextrin-containing composition and then mixing the *cannabis* plant extract or synthetic cannabinoid and the aqueous cyclodextrin-containing composition for a sufficient time to form complexes between the α-cyclodextrin and the cannabinoid(s) and/or terpene(s). The aqueous α-cyclodextrin-containing composition for use in the method may be an aqueous α-cyclodextrin-containing solution, slurry, or suspension.

Suitable oils for mixing with the *cannabis* plant extract or synthetic cannabinoid include non-toxic oils, such as edible oils, macerated oils, essential oils, and pharmaceutically acceptable oils. Examples of suitable edible oils include coconut oil, corn oil, olive oil, palm oil, cottonseed oil, peanut oil, rapeseed oil, safflower oil, sunflower oil, sesame oil, soybean oil, almond oil, pumpkin or squash seed oil, Brazil nut oil cashew oil, hazelnut oil, macadamia nut oil, pecan oil, pine nut oil, pistachio oil, walnut oil, citrus oils, carob oil, cocoa butter, shea butter, hemp oil, flaxseed oil, grapeseed oil, other seed oils. Examples of suitable macerated oils include *arnica* oil, calendula oil, carrot oil, chickweed oil, comfrey oil, galangal oil, horse chestnut oil, linden blossom oil, marigold oil, meadowsweet oil, mullein oil, sea weed oil, and St. John's Wort oil. Examples of suitable essential oils include bergamot oil, camphor oil, peppermint oil, *cannabis* flower essential oil, cardamom seed oil, cinnamon oil, citronella oil, coffee oil, *eucalyptus* oil, garlic oil, fennel seed oil, fenugreek oil, ginger oil, henna oil, jasmine oil, rose oil, rosehip oil, lavender oil, ylang-ylang oil, wintergreen oil, turmeric oil, thyme oil. Examples of pharmaceutically acceptable oils include ethyl butyrate, ethyl caprylate, ethyl oleate, triglycerides, and soybean oil.

Suitable alcohols for mixing with the *cannabis* plant extract or synthetic cannabinoid include alcohols that are suitable for food and/or natural products and/or pharmaceutical production. Examples of suitable alcohols are ethanol and isopropanol. The amount of alcohol added to the *cannabis* plant extract or synthetic cannabinoid is sufficient to make the *cannabis* plant extract or synthetic cannabinoid free flowing. The amount of alcohol added to the *cannabis* plant extract or synthetic cannabinoid may be up to 95% v/v, 90% v/v, 85% v/v, 80% v/v, 75% v/v, 70% v/v, 65% v/v, 60% v/v, 55% v/v, 50% v/v, or 45% v/v of the total volume of the alcohol and *cannabis* plant extract mixture. The *cannabis* plant extract or synthetic cannabinoid may be mixed with the alcohol before or after combining the extract or synthetic cannabinoid with an aqueous α-cyclodextrin-containing composition. Preferably the alcohol is mixed with the extract or synthetic cannabinoid before mixing the extract or synthetic cannabinoid with the aqueous α-cyclodextrin-containing composition, e.g., an aqueous solution, slurry, or suspension. The *cannabis* plant extract or synthetic cannabinoid may be mixed with an alcohol in a 1:15 w/v, 1:10 w/v, 1:5 w/v, 1:2 w/v ratio of extract to alcohol, and ranges there between.

Figure 1:
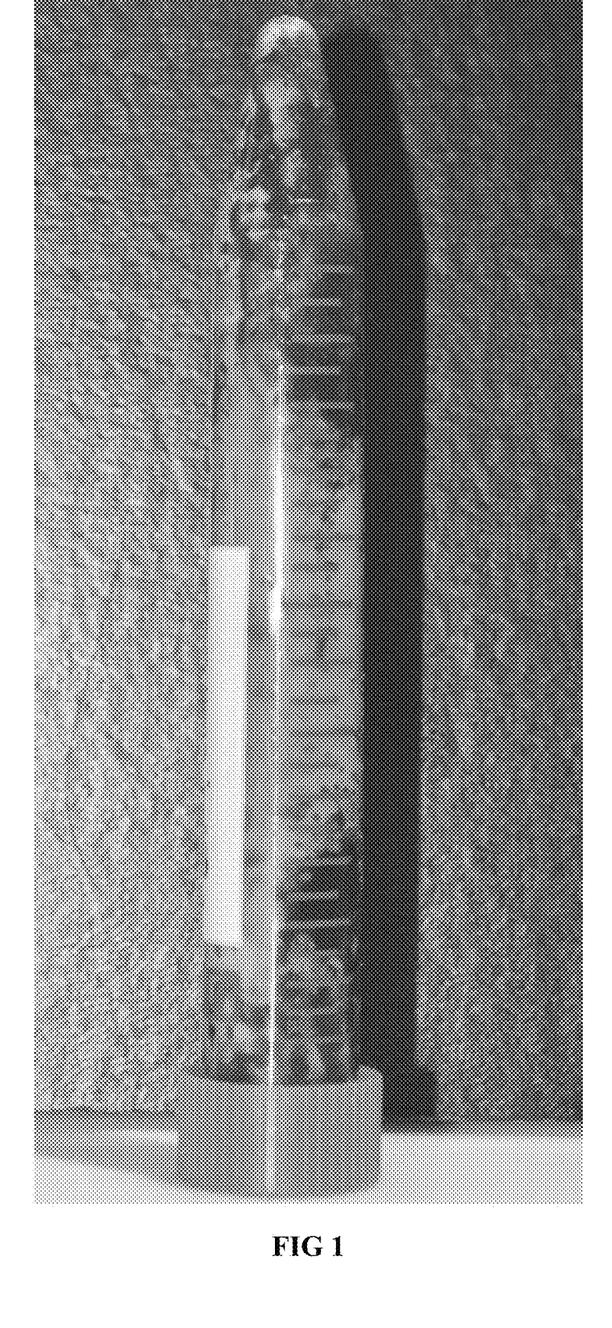
FIG. 1 depicts the results of adding an overly concentrated *cannabis* plant extract to a slurry of α-cyclodextrin in water.
Figure 2:
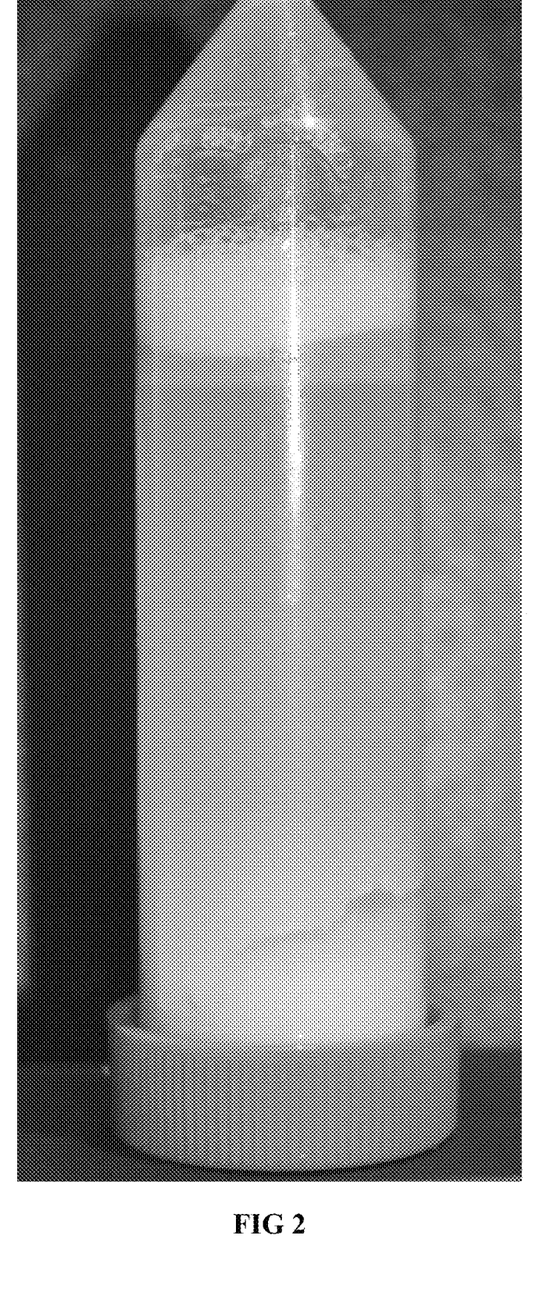
FIG. 2 depicts a commercially-available cannabinoid-containing oil diluted with vegetable oil when first mixed with a slurry of α-cyclodextrin and water.
Figure 3:
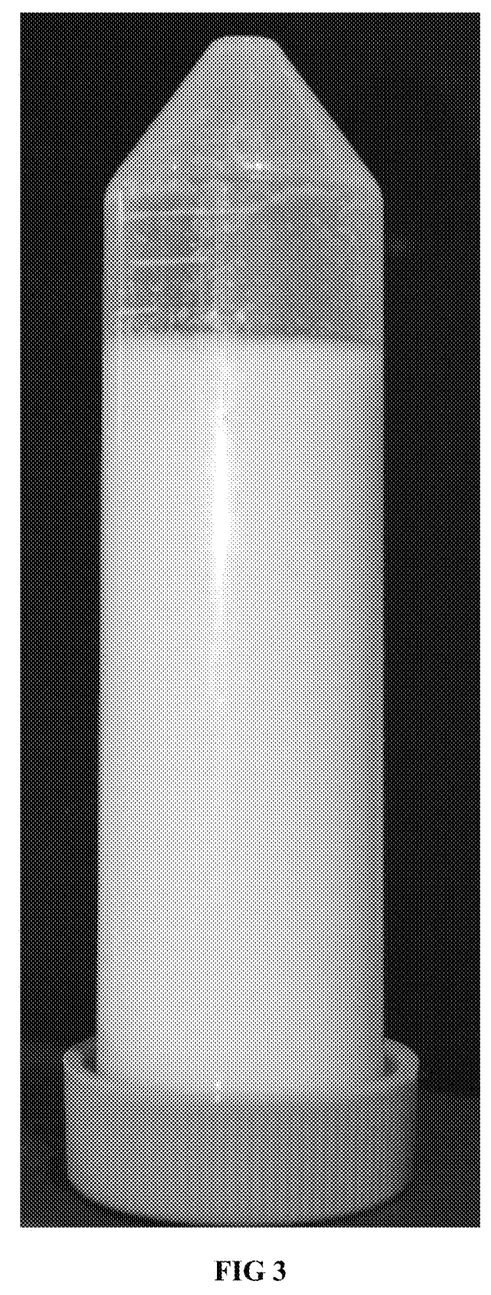
FIG. 3 depicts a commercially-available cannabinoid-containing oil diluted with vegetable oil mixed with a slurry of α-cyclodextrin in water after gentle mixing for several hours.

The effects of the consistency and/or viscosity of the plant extract in the methods of this invention are shown in FIGS. 1-3. As shown in FIG. 1, adding an overly concentrated tar-like cannabinoid-containing extract to an α-cyclodextrin slurry results in the tar-like material not being suspended in the α-cyclodextrin slurry. Instead, the tar-like material congeals into clumps of material that stick to the walls of the container (e.g., a tube). The clumps of material remain unchanged even after extensive mixing. In contrast, FIG. 2 shows a tube containing a commercially-available cannabinoid-containing oil diluted with vegetable oil when it is first mixed with an aqueous α-cyclodextrin containing slurry. As can be seen, undissolved α-cyclodextrin rests at the bottom of the tube while the middle portion of the tube contains an aqueous layer comprising both dissolved α-cyclodextrin and suspended undissolved α-cyclodextrin. The cannabinoid-containing oil appears to be distributed between the undissolved α-cyclodextrin layer and the top of the aqueous layer. Gentle mixing is used in order to avoid the formation of froth, as seen at the top of the container, and to avoid the formation of an emulsion. After gently mixing the tube for several hours the α-cyclodextrin/oil slurry mixture appears homogeneous and has a uniform off-white color (FIG. 3). Due to the gentle mixing, an emulsion is not formed and there is no froth at the top of the container. The aqueous mixture in the container is ready for using as a slurry in an edible product, e.g., a cupcake, and/or for drying, e.g., into a powder.

Figure 4A:
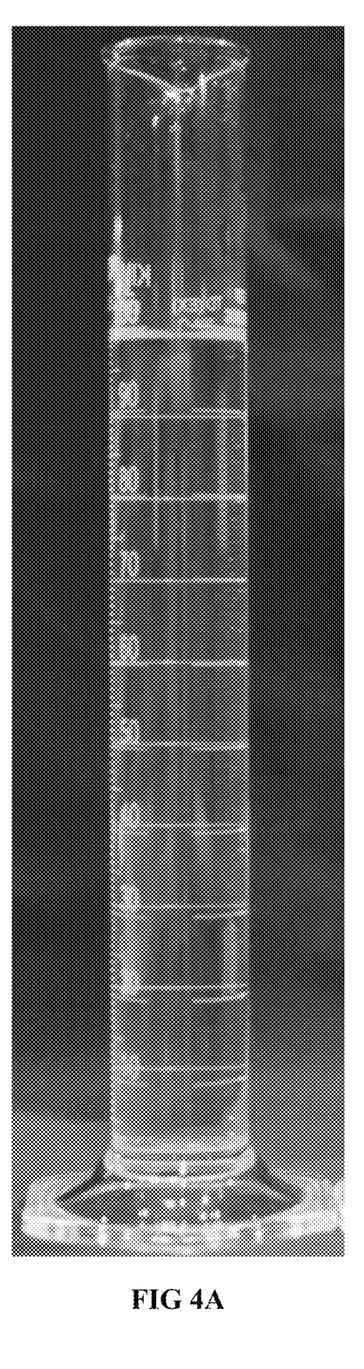
FIGS. 4A and 4B depict a comparison between water with (FIG. 4A) or without (FIG. 4B) the addition of a dried *cannabis* plant extract composition comprising THC and α-cyclodextrin prepared as described herein.
Figure 4B:
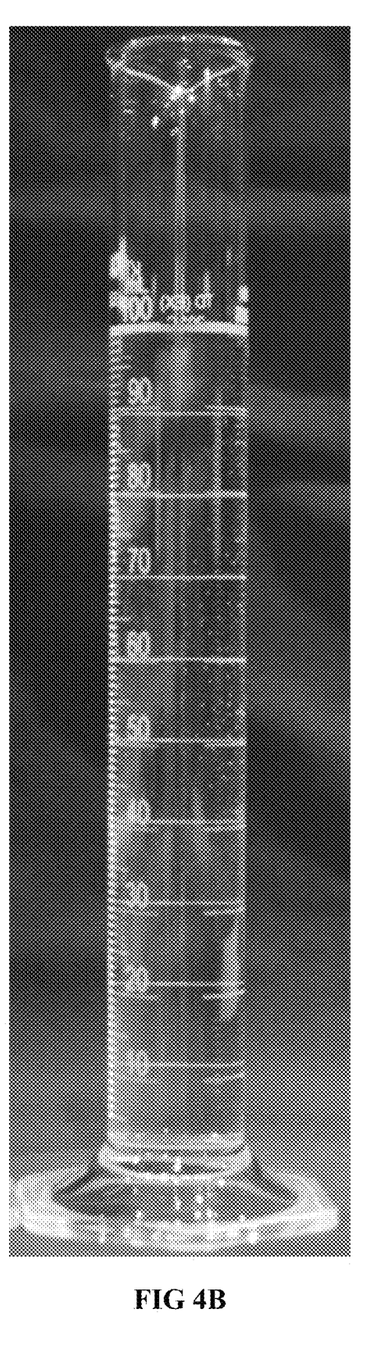

An embodiment of this invention is a *cannabis* plant extract-derived composition or synthetic cannabinoid-derived composition comprising complexes of cannabinoids and α-cyclodextrin that are water soluble. FIG. 4A depicts a graduated cylinder containing a mixture of 100 mL water and 863 mg of a dried *cannabis* plant extract-derived composition of this invention comprising 1 mg THC in complexes with α-cyclodextrin and FIG. 4B depicts a graduated cylinder with just 100 ml water. The mixture in FIG. 4A and the water in FIG. 4B are indistinguishable. The *cannabis* plant extract composition combined with water depicted in FIG. 4A was prepared from *cannabis* plant distillate.

An aspect of this invention is a *cannabis* plant extract-derived composition comprising water soluble complexes of α-cyclodextrin and terpenes; α-cyclodextrin and THC; α-cyclodextrin and CBD, or α-cyclodextrin and cannabinol, or mixtures of such complexes. Another aspect of the invention is a *cannabis* plant extract-derived composition comprising complexes selected from the group consisting of α-cyclodextrin and terpenes, α-cyclodextrin and THC, α-cyclodextrin and CBD, α-cyclodextrin and cannabinol, and mixtures of such complexes that are water soluble. An aspect of this invention is a synthetic cannabinoid-derived composition comprising water soluble complexes of α-cyclodextrin and one or more synthetic cannabinoids.

In one embodiment of the invention, the *cannabis* plant-derived composition or synthetic cannabinoid-derived composition of this invention is an aqueous solution, an aqueous slurry, or an aqueous suspension comprising complexes of α-cyclodextrin and cannabinoid(s) and/or complexes of α-cyclodextrin and terpene(s) or mixtures of such complexes.

In one embodiment of the invention, the *cannabis* plant-derived composition or synthetic cannabinoid-derived composition of this invention is a water-soluble powder comprising complexes of α-cyclodextrin and cannabinoid(s) and/or complexes of α-cyclodextrin and terpene(s) or mixtures of such complexes.

An embodiment of the invention is a liquid comprising the *cannabis* plant extract-derived composition or synthetic cannabinoid-derived composition described herein comprising complexes of α-cyclodextrin and cannabinoid(s) and/or complexes of α-cyclodextrin and terpene(s) or mixtures of such complexes. The liquid may be, e.g., water, a tea, a coffee, a juice, a carbonated beverage, or an alcoholic beverage.

Another aspect of the invention is a food product comprising a *cannabis* plant extract-derived composition or synthetic cannabinoid-derived composition of this invention such that the food comprises complexes of α-cyclodextrin and at least one cannabinoid and/or complexes of α-cyclodextrin and at least one terpene, or mixtures of such complexes. In one embodiment, the food product of the invention may comprise a sweetening agent, a coloring agent and/or a flavoring agent known in the art.

In one embodiment, the food product is a farinaceous food product or a confection. Examples of a farinaceous food product include, e.g., cake, muffin, brownie, cookie, cracker, doughnut, or biscuit. Examples of a confection include e.g., caramel, chocolate, nougat, chewing gum, toffee, lozenge, fondant, halvah, jelly, gelatin, candies, e.g., gummies (e.g., gummy bears), suckers or lollipops, licorice, marshmallow, taffy, or marzipan.

In another embodiment, the food product is a non-farinaceous food product. Examples of a non-farinaceous food product include e.g., a dairy product, a meat product, a fruit product, or a vegetable product. Preferred examples of a non-farinaceous food product include beverages, such as tea, herbal tea, coffee, juice, bottled water, a carbonated beverage, or an alcoholic beverage.

While *cannabis* plant-derived compositions and synthetic cannabinoid-derived compositions of this invention can be added to the food products in any amount, it is understood that a preferred amount would be such that the organoleptic properties between the food product with or without the *cannabis* plant-derived compositions or synthetic cannabinoid-derived compositions are not significantly different.

The *cannabis* plant extract-derived composition or synthetic cannabinoid-derived composition of this invention may be mixed with an edible oil, e.g., include coconut oil, corn oil, olive oil, palm oil, cottonseed oil, peanut oil, rapeseed oil, safflower oil, sunflower oil, sesame oil, soybean oil, almond oil, pumpkin or squash seed oil, Brazil nut oil cashew oil, hazelnut oil, macadamia nut oil, pecan oil, pine nut oil, pistachio oil, walnut oil, citrus oils, carob oil, cocoa butter, shea butter, hemp oil, flaxseed oil, grapeseed oil, other seed oils.

Another aspect of this invention is a method for increasing the content of THC and/or CBD and/or synthetic cannabinoid in a food product by adding the *cannabis* plant-derived composition or synthetic cannabinoid-derived composition of this invention to a food product in an amount sufficient to increase the THC and/or CBD and/or synthetic cannabinoid content of the food product.

The *cannabis* plant-derived composition or synthetic cannabinoid-derived composition of this invention may be added to the food product at any stage of its preparation. For example, a *cannabis* plant extract-derived composition or synthetic cannabinoid-derived composition described herein may be mixed with the food product's ingredients so that it is distributed throughout the food product and the product may then be cooked, or the composition may be mixed or added to the final food product. In some instances a *cannabis* plant extract-derived composition and synthetic cannabinoid-derived composition of this invention may be applied to the surface of the food product, e.g., as a glaze, icing, or coating, or the composition may be simply sprinkled on or mixed with the food product, e.g., stirred into a beverage, e.g., a tea, cocoa, coffee, juice, smoothie, or alcoholic beverage.

Another embodiment of the invention is a topical formulation comprising a *cannabis* plant extract-derived composition of this invention. An embodiment of this invention a topical formulation comprising a synthetic cannabinoid-derived compositions of this invention. The topical formulation may be, for example, a lotion, an oil, a topical gel, a spray, an ointment, or a cream comprising the *cannabis* plant extract-derived composition or synthetic cannabinoid-derived composition of this invention comprising complexes of α-cyclodextrin and at least one cannabinoid or complexes of α-cyclodextrin and at least one terpene, or comprising mixtures of such complexes. The topical formulation may include a compound which enhances absorption or penetration of the α-cyclodextrin complexes through the skin. Typical carriers include alcohol, water, mineral oil, liquid petrolatum, white petrolatum, glycerin, dimethylsulfoxide, polyethylene glycol and propylene glycol. The *cannabis* plant extract-derived composition or synthetic cannabinoid-derived composition of this invention may be added to the topical formulation at any stage of its preparation, e.g., the *cannabis* plant extract-derived composition or synthetic cannabinoid-derived composition may be mixed with the topical formulation's ingredients and then mixed together or the *cannabis* plant extract-derived composition or synthetic cannabinoid-derived composition may be mixed or added to the final topical formulation. The *cannabis* plant extract-derived composition or synthetic cannabinoid-derived composition of this invention may be mixed with an oil suitable for topical application, e.g., an essential oil, e.g., bergamot oil, camphor oil, peppermint oil, *cannabis* flower essential oil, cardamom seed oil, cinnamon oil, citronella oil, coffee oil, *eucalyptus* oil, garlic oil, fennel seed oil, fenugreek oil, ginger oil, henna oil, jasmine oil, rose oil, rosehip oil, lavender oil, ylang-ylang oil, wintergreen oil, turmeric oil, thyme oil.

In one embodiment, the topical formulation of this invention comprises complexes of α-cyclodextrin and cannabinoids, e.g., α-cyclodextrin and THC, α-cyclodextrin and CBD, α-cyclodextrin and cannabinol, or α-cyclodextrin and one or more synthetic cannabinoids, or mixtures thereof. In one embodiment, the topical formulation comprises complexes selected from the group consisting of THC-α-cyclodextrin complexes, CBD-α-cyclodextrin complexes, or cannabinol-α-cyclodextrin complexes, and mixtures thereof. In one embodiment, the topical formulation comprises complexes of α-cyclodextrin in complex with one or more of 1-pentyl-3-(1-naphthoyl)indole (JWH-018), 1-butyl-3-(1-naphthoyl)indole (JWH-073), 1-[2-(4-morpholinyl)ethyl]-3-(1-naphthoyl)indole (JWH-200), 5-(1,1-dimethylheptyl)-2-[(1R, 3 S)-3-hydroxycyclohexyl]-phenol (CP-47,497), and 5-(1,1-dimethyloctyl)-2-[(1R, 3 S)-3-hydroxycyclohexyl]-phenol (cannabicyclohexanol; CP-47,497 C8 homologue) and other CBD analogs (see e.g., Morales et al. Frontiers in Pharmacology 28 Jun. 2017 Vol 8, Article 422 p. 1-18), dronabinol, or nabilone. In one embodiment, the topical formulation comprises complexes of α-cyclodextrin in complex with one or more synthetic cannabinoids selected from the group consisting of 1-pentyl-3-(1-naphthoyl)indole (JWH-018), 1-butyl-3-(1-naphthoyl)indole (JWH-073), 1-[2-(4-morpholinyl)ethyl]-3-(1-naphthoyl)indole (JWH-200), 5-(1,1-dimethylheptyl)-2-[(1R, 3 S)-3-hydroxycyclohexyl]-phenol (CP-47,497), and 5-(1,1-dimethyloctyl)-2-[(1R, 3 S)-3-hydroxycyclohexyl]-phenol (cannabicyclohexanol; CP-47,497 C8 homologue), dronabinol, and nabilone.

An aspect of the invention is a method of alleviating pain in a subject in need thereof, comprising administering to the subject a therapeutically effective amount of a *cannabis* plant-derived composition or synthetic cannabinoid-derived composition of the invention described herein, comprising complexes of α-cyclodextrin and at least one cannabinoid (e.g., THC, CBD, and/or cannabinol or a synthetic cannabinoid). The *cannabis* plant-derived composition administered may also comprise complexes α-cyclodextrin and at least one terpene. A therapeutically effective amount of the *cannabis* plant-derived composition or the synthetic cannabinoid-derived composition in this embodiment is an amount sufficient to alleviate pain in the subject in need thereof. The subject in need thereof is a subject, e.g. a human, horse, cow sheep, goat, dog, cat, rat or mouse, suffering from pain.

An aspect of the invention is a method of alleviating anxiety in a subject in need thereof, comprising administering a therapeutically effective amount of a *cannabis* plant-derived composition or synthetic cannabinoid-derived composition of the invention described herein comprising complexes of α-cyclodextrin and at least one terpene and/or α-cyclodextrin and at least one cannabinoid (e.g., THC, CBD, and/or cannabinol, or synthetic cannabinoid) to the subject. A therapeutically effective amount of the composition of this invention is an amount sufficient to alleviate anxiety in the subject in need thereof. The subject in need thereof is a subject, e.g. a human, horse, cow sheep, goat, dog, cat, rat or mouse, suffering from anxiety.

An aspect of the invention is a method of increasing feelings of well-being and relaxation in a subject comprising administering a sufficient amount of a *cannabis* plant-derived composition or synthetic cannabinoid-derived composition of the invention comprising complexes of α-cyclodextrin and at least one terpene and/or α-cyclodextrin and at least one cannabinoid (e.g., THC, CBD, and/or cannabinol, or synthetic cannabinoid) to the subject. A sufficient amount of the compositions of this invention is an amount sufficient to increase feelings of well-being and relaxation in the subject.

Another aspect of the invention is a method of treating a subject, e.g. a human, a non-human primate, a horse, cow sheep, goat, dog, cat, rat or mouse, having a disorder having symptoms that are alleviated by treatment with a cannabinoid. The method comprises administering a therapeutically effective amount of a *cannabis* plant-derived composition or synthetic cannabinoid-derived composition of the invention comprising complexes of α-cyclodextrin and at least one terpene and/or α-cyclodextrin and at least one cannabinoid (e.g., THC, CBD, and/or cannabinol and/or a synthetic cannabinoid) to the subject having the disorder. In an aspect of the invention, the composition of this invention administered to the subject comprises complexes of α-cyclodextrin and cannabinoids (e.g., THC, CBD, cannabinol, and synthetic cannabinoids). Examples of disorders that can be treated with the compositions described herein include trigeminal neuralgia, agitation, Alzheimer's dementia, anxiety disorders, jet lag, depression, anorexia, Attention Deficit Disorder (ADD) with or without hyperactivity, Autism Spectrum Disorder (ASD), cachexia, cancer, chronic cluster headaches, Crohn's disease, convulsions, epilepsy, gastrointestinal tract distress (e.g., heartburn indigestion, stomach ache), glaucoma, HIV/AIDS, Huntington's disease, inflammation (chronic or acute), inflammatory bowel disease, irritable bowel syndrome (IBS) with or without diarrhea or constipation, migraine headaches whether hormone mediated or not, muscle spasms, nausea, neurodegenerative diseases including Lou Gehrig's disease, all forms of pain (e.g., acute, chronic, neuropathic, trigeminal nerve pain, pain associated with or accompanying migraine headaches and cancer), Parkinson's disease and Parkinsonian-type symptoms, spinal-cord injuries, postmenstrual syndrome (PMS), Post-Traumatic Stress Disorder (PTSD), seasonal affective disorder (SAD), seizures, seizures associated with Lennox-Gastaut syndrome or Dravet syndrome, sleep disorders such as insomnia, spasticity from multiple sclerosis, ulcerative colitis, and vomiting. An embodiment of this invention is a method for treating a subject, e.g. a human, having cancer, chronic cluster headaches, Crohn's disease, convulsions, epilepsy, glaucoma, migraine headaches whether hormone mediated or not, nausea, or trigeminal nerve pain by administering to the subject a therapeutically effective amount of a *cannabis* plant extract-derived composition or synthetic cannabinoid-derived composition of this invention.

Treatment of a disorder as described herein refers to reducing or eliminating one or more symptoms of the disorder. A therapeutically effective amount of a composition of this invention as described herein for treating a disorder is an amount sufficient to reduce or eliminate one or more symptoms of the disorder. For example, if a subject has a disorder that is associated with pain, a therapeutically effective amount is an amount sufficient to reduce or eliminate the pain. For example, if the disorder is an anxiety disorder a therapeutically effective amount is an amount sufficient to reduce or eliminate anxiety.

A therapeutically effective amount of a *cannabis* plant-derived composition or synthetic cannabinoid-derived composition of the invention described herein, comprising complexes of α-cyclodextrin and at least one cannabinoid (e.g., THC, CBD, and/or cannabinol or a synthetic cannabinoid) administered to a subject, e.g. a subject having anxiety, pain or another disorder having symptoms that are alleviated by treatment with a cannabinoid, may be administered to the subject in any suitable form, e.g., a tablet, capsule, pill, elixir, wafer, beverage or a food product.

The compositions of this invention may be administered to the subject by any suitable method, e.g., orally (swallowed), sublingually (under the tongue), transdermally, transmucosally, intranasally, topically, or rectally, in an amount suitable to achieve the desired effects.

It has been found that the cannabinoids and/or terpenes complexed with α-cyclodextrin in the compositions of this invention are absorbed more rapidly through the mucosal membranes of a subject than are cannabinoids and/or terpenes that are not complexed with α-cyclodextrin. Moreover, the effects of the cannabinoids in the α-cyclodextrin complexes in the *cannabis* plant extract-derived compositions and synthetic cannabinoid-derived compositions of this invention are prolonged as compared to the effects of the cannabinoids in the untreated *cannabis* plant extracts or synthetic cannabinoids. Without wishing to be bound by theory, it is contemplated that the α-cyclodextrin and cannabinoid complexes are amphiphilic and are thereby absorbed more readily through a mucosal membrane. It is also contemplated that at least a portion of the complexes are delivered to the subject's stomach and intestines where the cannabinoids are released thereby prolonging their effect on the subject. An embodiment of this invention is a composition comprising cannabinoids formulated to enhance absorption of the cannabinoids through mucosal membranes of a subject, and/or to prolong the effect of the cannabinoids on the subject, wherein the cannabinoids are in the form of complexes with α-cyclodextrin.

An embodiment of this invention is a method for enhancing the absorption of cannabinoids and/or terpenes in a *cannabis* plant extract or absorption of synthetic cannabinoids through mucosal membrane of a subject by mixing the *cannabis* plant extract and synthetic cannabinoids with an aqueous α-cyclodextrin-containing composition under conditions suitable to form complexes of α-cyclodextrin and the cannabinoids and/or terpenes, or both. The resulting composition comprising the complexes may be administered to the subject or the complexes in the mixture may then be collected, e.g., by filtering the mixture, or drying the mixture, and then administered to the subject.

EXAMPLES

Example 1—Tasteless, Odorless *Cannabis* Powder

A high CBD-containing *cannabis* viscous oil was diluted 1:15 (w/v) with either ethyl or isopropyl alcohol and gently mixed using a tube rocking apparatus, for up to 3 hours to make the viscous oil less viscous. An α-cyclodextrin slurry was prepared by adding 900 mg of α-cyclodextrin to 10 mL of a 10% (w/v) aqueous α-cyclodextrin solution. 600 μL of the above-mentioned alcohol diluted *cannabis* viscous oils was added to the aqueous α-cyclodextrin slurry to form suspensions. The suspensions were shaken vigorously by hand for 30 seconds and then gently mixed at ambient temperature for at least 1 hour or until all visible signs of the deep green diluted viscous oil disappear. The suspensions were shaken vigorously by hand for a few seconds and then poured into an evaporating dish. The suspensions were dried at ambient temperatures for at least 48 hours or at 90-120° C. for 1-3 hours, scraped into a mortar, and ground to a fine greenish-tinged off-white powder. The powder was odorless, tasteless, and water soluble. Recovery based upon the quantity of solids in the initial mix of oil and α-cyclodextrin slurry was near 100%.

Example 2—Tasteless, Odorless *Cannabis* Powder

A commercially-available cannabinoid oil [Tweed https://www.tweed.com] that had been diluted with vegetable oil by the supplier to contain 5.16 mg/mL THC and 4.77 mg/mL CBD was made into an off-white tasteless and odorless powder as follows. 600 mg of α-cyclodextrin was suspended in 7 mL of 10% (w/v) α-cyclodextrin in water. To this α-cyclodextrin suspension, 420 μL of the commercially available cannabinoid oil was added and briefly shaken by hand. The suspension was then mixed gently overnight or until all signs of the oil disappeared and the suspension appeared homogenous. The homogenous suspension was transferred to an evaporating dish and dried at ambient temperature for 48-72 hours. The dried material was transferred to a mortar and ground to an off-white waxy powder. At least a portion of this material was not soluble in cold water and formed small oil droplets in hot water. However, this material was tasteless and odorless. Analysis of the commercially available cannabinoid oil demonstrated that 2.0 mg of CBD and 2.17 mg of THC were added to the α-cyclodextrin suspension. Analysis of the off-white waxy powder generated by the method demonstrated 0.12% (w/w) THC and 0.13% (w/w) CBD. Recovery based upon total solids was near 100%.

Example 3—Tasteless, Odorless *Cannabis* Suspension for Baking 3.0 mL of a commercially-available *cannabis* oil (Spectrum Cannabis, https://spectrum Cannabis.com) containing 25 mg/mL THC was added to 45 mL of water containing 9.5 g α-cyclodextrin powder to make a suspension. The suspension was shaken vigorously by hand for one minute and then gently rocked for 3 hours. The resulting slurry was then added to a commercially available cupcake mix (e.g., Betty Crocker Vanilla Butter Cream) as a direct substitute for the same amount of water required by the manufacturer's cupcake recipe. As instructed by the cupcake recipe, the batter was divided into 12 equal portions and baked as indicated by the cupcake recipe. The olfactory and organoleptic properties of the resulting cupcakes were indiscernible from those of cupcakes prepared according to the unaltered cupcake recipe.

Example 4—Tasteless, Odorless, High CBD-Containing Beverage

High CBD *cannabis* containing viscous oil (50.9 mg CBD/100 mg oil) was diluted 1:15 (w/v) with isopropyl alcohol with gentle rocking until the oil was totally dissolved. The diluted oil (1.6 mL) was added to 10% (w/v) α-cyclodextrin aqueous solution (40 mL) containing additional solid α-cyclodextrin (8 g). The suspension was briefly mixed vigorously by hand before being rocked gently for 3-4 hours. The resulting homogeneous-appearing slurry was poured into a drying dish, and the solvents in the slurry were evaporated over several hours at approximately 110° C. Off-white crystalline material was recovered, and the yield (based on the measured amount of cannabinoid in the diluted oil) based on total mass of solids was 97%. The off-white crystalline material was transferred to a mortar and ground to a fine off-white powder. Analysis of the powder indicated that the powder contained 0.46% (w/w) CBD. The off-white powder (1.3 g of powder, the equivalent of 6 mg CBD) was dissolved in water (500 mL). The resulting solution was filtered through filter paper to remove traces of green material, believed to be vegetable matter. Although the resulting solution had a slight opalescence, the solution was transparent and tasteless. A volunteer suffering from chronic trigeminal nerve facial pain consumed approximately one-third of the CBD-containing solution. The volunteer reported pain relief within 10-15 minutes and reported that the relief lasted for over 4 hours after consuming the CBD-containing solution.

Example 5—Tasteless, Odorless, High THC-Containing Iced Tea Beverage

The procedure used to make a high THC iced tea beverage was similar to the procedure used in Example 4. A THC-containing powder was prepared from a high THC-containing distillate as set forth in Example 4 and a sufficient amount of the powder was mixed with an iced tea beverage such that the resulting iced tea beverage contained 2.5 mg THC in 341 ml. Eight volunteers, two suffering from anxiety (group 1), three suffering from headaches (group 2) and three having neither headaches of anxiety (group 3), consumed 341 ml of the iced tea beverage and reported rapid onset of the desired effects, i.e., reduction of anxiety (group 1), reduction of headache (group 2) and an enhanced relaxation, happiness, and heightened sensory perception (groups 1, 2 and 3) that persisted for more than 2.5 hours.

None of the eight volunteers reported detecting any *cannabis* and/or terpene taste or odor typically associated with *cannabis* extract in the iced tea beverage. The volunteers reported that they only detected the flavor and odor of the tea in the iced tea beverage.

Example 6—Preparing Tasteless, Odorless *Cannabis* Powder from a *Cannabis* Oil

High CBD containing *cannabis* extract with the consistency of a tar was diluted 1:15 (w/v), with isopropyl alcohol and gently mixed by rocking the tube on a rocking apparatus for up to 3 hours to make the tar less viscous. An α-cyclodextrin slurry was prepared by adding 12 g of α-cyclodextrin to 40 mL of water followed by vigorous shaking by hand for 2 minutes. 1.6 mL of the above-mentioned alcohol diluted *cannabis* tar was added to the aqueous α-cyclodextrin slurry to form a suspension. This suspension was shaken vigorously by hand for 30 seconds and then gently mixed for at least 1 hour or until all visible signs of the deep green diluted tar disappear. The suspension was shaken vigorously by hand for a few seconds and then poured into an evaporating dish. The suspension was dried at ambient temperature for at least 48 hours, scraped into a mortar, and ground to a fine off-white powder. The yield, based upon solids added, was near 100%.

Example 7—Tasteless, Odorless, Water-Soluble THC-Containing *Cannabis* Powder

A commercially available THC distillate (300 mg) (https://www.thconcentrates.ca) was diluted with isopropyl alcohol (4.2 mL). The diluted distillate (1.6 mL) was added to 40 mL of water containing 10 g of α-cyclodextrin. The resulting suspension was shaken vigorously by hand in order to evenly distribute the diluted distillate throughout the suspension. The suspension was then rocked gently for 3 hours before being transferred to a drying dish. The suspension was dried at ambient temperature for at least 48 hours to yield a powder containing 11.6 mg THC per 1 g powder.

Example 8—Tasteless, Odorless, THC Water Beverage

The powder of Example 7 (435 mg) was dissolved in 500 ml water. Brief mixing produced a tasteless, odorless THC-containing water beverage containing 5 mg THC.

Example 9—Tasteless, Odorless, THC-Containing Tea Beverage

The powder of Example 7 (174 mg) was added to a tea cup containing one tea bag of commercially available herbal tea (Stress Buster, www.tealish.com). The powder dissolved completely upon addition of boiling water (250 mL). After steeping the tea bag for 5 minutes, an herbal tea beverage containing 2 mg THC was produced.

THC-containing *cannabis* powders were prepared by mixing various ratios of THC distillate, commercially available from, e.g., https://www.thconcentrates.ca, and α-cyclodextrin. The THC distillate (300 mg) was diluted with isopropyl alcohol (4.2 mL) and then added to an α-cyclodextrin aqueous solution to generate suspensions having a ratio of α-cyclodextrin to THC distillate of 70:1, 87:1, 105:1 and 122:1. The resulting suspensions were shaken vigorously by hand in order to evenly distribute the diluted distillate throughout the suspensions. The suspensions were then rocked gently for 3 hours before being transferred to a drying dish. The suspensions were dried at ambient temperature for 48-72 hours or at 90-120° C. for 1-3 hours. Sufficient amounts of each resulting powder were added to water to produce solutions having a THC concentration of 10 mg/L. The solutions were then tasted by volunteers. The results are presented in Table 1. Table 1 recites the ratios of α-cyclodextrin (α-CD) to THC distillate and the taste characteristics of THC-containing solutions. All the solutions showed opalescence that decreased as the percent α-cyclodextrin increased and the ratio of α-cyclodextrin to distillate increased.

TABLE 1

| % α-CD | α-CD: Isopropanol | α-CD: THC Distillate | Solution Characteristics |
|---|---|---|---|
| 20 | 0.20 | 70:1 | Slight "off" taste, like stale water, with a thin and sparse layer on top of water |
| 25 | 0.16 | 87:1 | No taste, small film on surface of water |
| 30 | 0.13 | 105:1 | No taste, all solid material dissolved |
| 35 | 0.11 | 122:1 | No taste, all solid material dissolved |

The following Table 2 provides examples of *cannabis* plant extract-derived compositions prepared from different *cannabis* plant extracts, i.e., a tar, a distillate or an oil according to methods of the invention. "% Starting Material" in Table 2 refers to the approximate % mass (tar) or volume (distillate or oil) of the original tar, distillate, or oil mixed with an aqueous α-cyclodextrin composition. "% α-CD" is the % of α-cyclodextrin by weight in the aqueous cyclodextrin-containing composition mixed with the *cannabis* plant extract. "End Product" means the *cannabis* plant extract-derived composition produced by treating the plant extract with the aqueous α-cyclodextrin composition as described herein and dried to a powder form or not dried such that the end-product is in the form of a slurry.

TABLE 2

| | Staring Material | End Product | % α-CD | % Starting Material |
|---|---|---|---|---|
| 1 | Tar | Powder | 30 | 0.3 |
| 2 | Distillate | Powder | 25 | 0.3 |
| 3 | Commercial Oil | Slurry | 21 | 6.7 |

The foregoing description and examples have been set forth merely to illustrate the invention and are not meant to be limiting. Since modifications of the described embodiments incorporating the spirit and the substance of the invention may occur to persons skilled in the art, the invention should be construed broadly to include all variations within the scope of the claims and equivalents thereof.

The invention claimed is:

1. A method for making a composition comprising complexes of α-cyclodextrin and one or more cannabinoids, complexes of α-cyclodextrin and one or more terpenes, or complexes of α-cyclodextrin and one or more cannabinoids and one or more terpenes, the method comprising the steps of:

(a) combining a first composition comprising one or more cannabinoids, one or more terpenes, or one or more cannabinoids and one or more terpenes with an aqueous composition consisting essentially of α-cyclodextrin; and (b) mixing the first composition and the aqueous composition consisting essentially of α-cyclodextrin for a sufficient time to form complexes between the α-cyclodextrin and one or more cannabinoids, complexes between the α-cyclodextrin and one or more terpenes, or complexes between the α-cyclodextrin and one or more cannabinoids and one or more terpenes, wherein the ratio of α-cyclodextrin to the first composition is at least about 70:1 (w/w), and wherein the composition does not comprise an amylase or amylase-like enzyme.

2. The method of claim 1, further comprising the step of:
(c) drying the mixture from step (b).

3. The method of claim 1, wherein the first composition is a *cannabis* plant extract comprising one or more phytocannabinoids or a composition comprising one or more synthetically produced cannabinoids.

4. The method of claim 3, wherein the phytocannabinoid is THC, CBD, cannabinol, or mixtures thereof and wherein the synthetic cannabinoid is 1-pentyl-3-(1-naphthoyl)indole (JWH-018), 1-butyl-3-(1-naphthoyl)indole (JWH-073), 1-[2-(4-morpholinyl)ethyl]-3-(1-naphthoyl)indole (JWH-200), 5-(1,1-dimethylheptyl)-2-[(1R, 3S)-3-hydroxycyclohexyl]-phenol (CP-47,497), and 5-(1,1-dimethyloctyl)-2-[(1R, 3S)-3-hydroxycyclohexyl]-phenol (cannabicyclohexanol; CP-47,497 C8 homologue) dronabinol, nabilone, or mixtures thereof.

5. The method of claim 1, wherein the aqueous α-cyclodextrin-containing composition is an aqueous solution, an aqueous slurry, or an aqueous suspension.

6. The method of claim 1, wherein the α-cyclodextrin solution comprises about 15% w/v to about 40% w/v α-cyclodextrin.

7. The method of claim 2, wherein the mixture is dried by evaporating the mixture in dishes or pans at ambient or moderately elevated temperatures, under atmospheric or reduced pressure, or in a rotary evaporator, by freeze drying or lyophilization, or by spray drying.

8. A method for complexing compounds in a *Cannabis* plant extract with α-cyclodextrin comprising the steps of:
(a) combining a *Cannabis* plant extract with an aqueous composition consisting essentially of α-cyclodextrin to produce a mixture,
(b) mixing the mixture from step (a) for sufficient time to form a composition comprising complexes of α-cyclodextrin with the compounds, wherein the compounds are cannabinoids, terpenes, or cannabinoids and terpenes, wherein the ratio of α-cyclodextrin to the *Cannabis* plant extract is at least about 70:1 (w/w), and wherein the composition does not comprise an amylase or amylase-like enzyme.

9. The method of claim 8, wherein the compound is a cannabinoid selected from the group consisting of cannabinol, THC, and CBD.

10. A method for increasing the THC and/or CBD and/or synthetic cannabinoid content of a food product comprising adding a composition comprising complexes of α-cyclodextrin and a phytocannabinoid, complexes of α-cyclodextrin and a synthetically produced cannabinoid, complexes of α-cyclodextrin and terpenes, or mixtures of two or more of such complexes, formulated such that the complexes are water soluble in the food product, wherein the composition does not comprise an amylase or amylase-like enzyme.

* * * * *